United States Patent
Sun et al.

(10) Patent No.: US 10,150,770 B2
(45) Date of Patent: Dec. 11, 2018

(54) CRYSTAL FORM OF BISULFATE OF JAK INHIBITOR AND PREPARATION METHOD THEREFOR

(71) Applicant: Jiangsu Hengrui Medicine Co., Ltd., Lianyungang, Jiangsu (CN)

(72) Inventors: Piaoyang Sun, Jiangsu (CN); Guaili Wu, Jiangsu (CN); Xiaohui Gao, Jiangsu (CN); Yongjiang Chen, Jiangsu (CN); Lingjia Shen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 36 days.

(21) Appl. No.: 15/516,529

(22) PCT Filed: Sep. 9, 2015

(86) PCT No.: PCT/CN2015/089223
§ 371 (c)(1),
(2) Date: Apr. 3, 2017

(87) PCT Pub. No.: WO2016/054959
PCT Pub. Date: Apr. 14, 2016

(65) Prior Publication Data
US 2018/0237438 A1 Aug. 23, 2018

(30) Foreign Application Priority Data
Oct. 9, 2014 (CN) .......................... 2014 1 0529863

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01); *C07B 2200/13* (2013.01)

(58) Field of Classification Search
CPC .................................................. C07D 487/04
USPC ..................................................... 514/265.1
See application file for complete search history.

(56) References Cited

FOREIGN PATENT DOCUMENTS

| CN | 1439010 A | 8/2003 |
|---|---|---|
| CN | 1798559 A | 7/2006 |
| WO | 2013091539 A1 | 6/2013 |
| WO | 2014194741 A1 | 12/2014 |

OTHER PUBLICATIONS

Int'l Search Report dated Dec. 2, 2015 in Int'l Application No. PCT/CN2015/089223.

*Primary Examiner* — Kahsay Habte
(74) *Attorney, Agent, or Firm* — Panitch Schwarze Belisario & Nadel LLP

(57) ABSTRACT

A crystal form I of a Janus Kinase (JAK) inhibitor (3aR,5s,6aS)—N-(3-methoxyl-1,2,4-thiadiazole-5-yl)-5-(methyl (7H-pyrrolo[2,3-d]pyrimidine-4-yl)amino)hexahydrocyclopenta[c]pyrrole-2(1H)-formamide bisulfate of formula (I) is provided. Also provided is a method of preparing the crystal form I of the JAK inhibitor of formula (I). The preparation method includes crystallizing any crystal form or amorphous compound solid of formula (I) in a single organic solvent to obtain the form I crystal. The crystal form I has excellent crystal stability and chemical stability. Additionally, the crystal solvent used to produce the crystal form I has low toxicity and a relatively low content of residual solvent, making the compound better suited for clinical treatment.

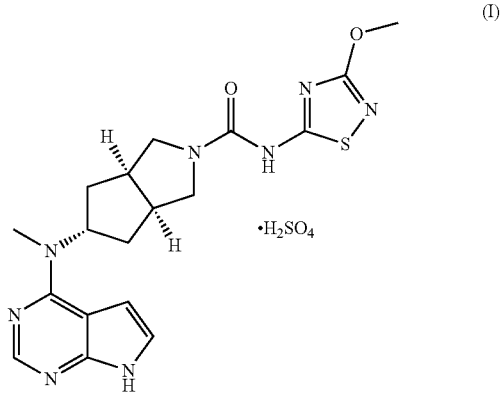

17 Claims, 4 Drawing Sheets

CRYSTAL FORM OF BISULFATE OF JAK INHIBITOR AND PREPARATION METHOD THEREFOR

CROSS-REFERENCE TO RELATED APPLICATION

This application is a Section 371 of International Application No. PCT/CN2015/089223, filed Sep. 9, 2015, which was published in the Chinese language on Apr. 14, 2016, under International Publication No. WO 2016/054959 A1, and the disclosure of which is incorporated herein by reference.

FIELD OF THE INVENTION

The present invention relates to crystal form I of (3aR, 5s,6aS)—N-(3-methoxyl-1,2,4-thiadiazole-5-yl)-5-(methyl (7H-pyrrolo[2,3-d]pyrimidine-4-yl)amino)hexahydrocyclopenta[c]pyrrole-2(1H)-formamide bisulfate and the preparation method and use thereof. The compound of formula (I) prepared according to the method of the present invention can be used for the treatment of arthritis.

BACKGROUND OF THE INVENTION

Arthritis is the most common chronic diseases in the world. There are many causes of arthritis, and the joint damage caused by arthritis is also different. Currently, Tofacitinib (CP-690550) is a novel oral JAK (Janus Kinase) pathway inhibitor developed by Pfizer Inc., and Tofacitinib is a first-in-class drug developed for rheumatoid arthritis treatment. Since Tofacitinib was produced in Pfizer's laboratories, the drug was highly expected to be a blockbuster drug. The success of the drug will be a big victory for the widely criticized research and development business of Pfizer. The results of Phase III clinical trials showed that the efficacy of Pfizer's Tofacitinib was significantly better than that of methotrexate.

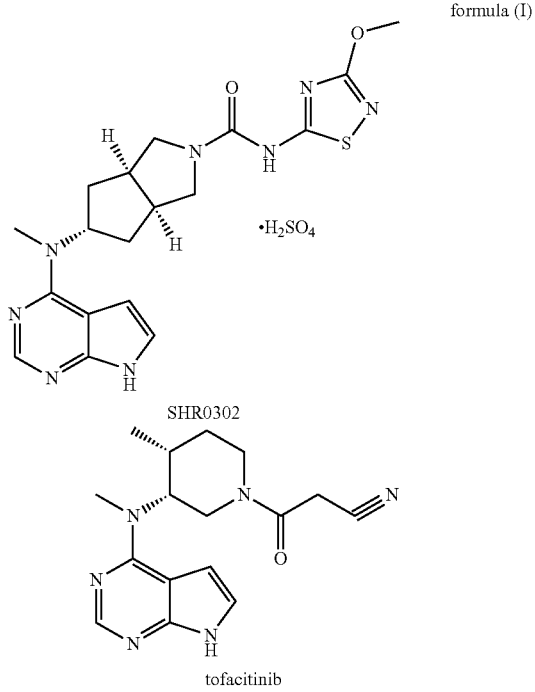

Based on the structure of Tofacitinib, a series of JAK inhibitor compounds, which are active in vitro and in vivo and are highly absorbable, have been developed. See WO2013091539. The compounds disclosed in WO2013091539 were screened and prepared as salts in which (3aR,5s,6aS)—N-(3-methoxyl-1,2,4-thiadiazole-5-yl)-5-(methyl(7H-pyrrolo[2,3-d]pyrimidine-4-yl)amino) hexahydrocyclopenta[c]pyrrole-2(1H)-formamide bisulfate of formula (I) was obtained, and its preparation method was disclosed in PCT Patent Application No. PCT/CN2014/076794 (an application previously filed by the applicant). The compound of formula (I) is expected to be a preferred compound of JAK inhibitors, and has important study significance for the treatment of rheumatic and rheumatoid arthritis.

The crystal structure of the pharmaceutically active ingredient often affects the chemical stability of the drug. Different crystallization conditions and storage conditions can lead to changes in the crystal structure of the compound, and sometimes the accompanying production of other forms of crystal form. In general, an amorphous drug product does not have a regular crystal structure, and often has other defects such as poor product stability, smaller particle size, difficult filtration, easy agglomeration, and poor liquidity. Thus, it is necessary to improve the various properties of the above product. There is a need to identify a new crystal form with high purity and good chemical stability.

SUMMARY OF THE INVENTION

The purpose of the present invention is to provide a stable crystal form of the compound of formula (I) and a preparation method thereof.

The inventor tested a series of crystal products of the compound of formula (I) obtained under various crystallization conditions by X-ray diffraction and differential scanning calorimetry (DSC) measurement. It was found that a stable crystal form of the compound of formula (I), which is referred to as crystal form I, can be obtained under normal crystallization conditions. The DSC spectrum of crystal form I of the compound of formula (I) according to the present invention has a melting endothermic peak at about 220° C. The X-ray powder diffraction spectrum, which is obtained by using Cu-Ka radiation and represented by 2θ angle and interplanar distance (d value), is shown in FIG. 1 in which there are characteristic peaks at 6.38 (13.85), 10.38 (8.51), 10.75 (8.23), 14.49 (6.11), 15.07 (5.88), 15.58 (5.69), 16.23 (5.46), 17.84 (4.97), 18.81 (4.72), 19.97 (4.44), 20.77 (4.27), 22.12 (4.02), 23.19 (3.83), 24.12 (3.69), 25.51 (3.49), 26.62 (3.35), 27.38 (3.26), 28.56 (3.12), and 29.91 (2.99).

In the preparation method of crystal form I of the present invention, the existing form of the compound of formula (I) used as a starting material is not particularly limited, and any crystal form or amorphous solid may be used. The preparation method of crystal form I of the compound of formula (I) of the present invention comprises:

using some lower organic solvents, preferably alcohols having 3 or less carbon atoms, and more preferably methanol as recrystallization solvents.

Specifically, the present invention provides a preparation method of crystal form I of the compound of formula (I) comprising the following steps of:

(1) dissolving a solid of the compound of formula (I) in any form into an appropriate amount of organic solvent under heating, then evaporating part of the solvent;

(2) filtering the resulting crystal, then washing and drying it.

In a preferred embodiment of the present invention, the organic solvent in step (1) is an alcohol having 3 or less carbon atoms, further preferably, the organic solvent is methanol.

The recrystallization method is different from the conventional recrystallization method. Any form of the compound of formula (I) is dissolved into an organic solvent under heating, and then part of the solvent is evaporated at atmospheric pressure. After completion of crystallization, the resulting crystal was filtered and dried to obtain the desired crystal. The crystal obtained by filtration is usually dried under vacuum at about 30 to 100° C., preferably 40 to 60° C., to remove the recrystallization solvent.

The crystal form of the obtained compound of formula (I) is determined by DSC and X-ray diffraction spectrum. Meanwhile, the residual solvent of the obtained crystal is also determined.

Crystal form I of the compound of formula (I) prepared according to a method of the invention does not contain or contains only a relatively low content of residual solvent, which meets the requirement of the National Pharmacopoeia concerning the limitation of the residual solvent of drug products. Thus, the crystal of the present invention is suitable for use as a pharmaceutically active ingredient.

The present invention also provides a pharmaceutical composition comprising crystal form I of the compound of formula (I) and at least one pharmaceutically acceptable carrier. The pharmaceutically acceptable carrier is selected from at least one of lactose, mannitol, microcrystalline cellulose, croscarmellose sodium, sodium carboxymethyl starch, hydroxypropyl methyl cellulose, povidone, and magnesium stearate. The content of crystal form I in the pharmaceutical composition of the present invention is 0.5 mg to 200 mg.

The present invention further relates to use of crystal form I of the compound of formula (I) or the pharmaceutical composition of the present invention in the preparation of a medicament for the treatment of JAK-related disease, preferably rheumatic and rheumatoid arthritis.

DETAILED DESCRIPTION OF THE INVENTION

The present invention is illustrated by the following examples in detail, but the examples of the invention are only intended to describe the technical solution of the invention, and should not be considered as limiting the scope of the present invention.

Test Instruments Used in the Experiments
1. DSC spectrum
Instrument type: Mettler Toledo DSC 1 Stare$^e$ System
Purging gas: Nitrogen
Heating rate: 10.0° C./min
Temperature range: 40-300° C.

2. X-ray diffraction spectrum
Instrument type: D/Max-RA Japan rigaku X-ray powder diffractometer
Rays: monochromatic Cu-Kα rays (λ=1.5418 Å)
Scanning mode: θ/2θ, Angular range: 2-40°
Voltage: 40 KV Electric Current: 40 mA Example 1: The Sample of the Compound of Formula (I) was Prepared According to the Method of Example 2 of PCT Patent Application No. PCT/CN2014/076794

Preparation of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate of Formula (I)

140 g (0.34 mol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide, 350 g of anhydrous methanol and 2.0 kg of dichloromethane were added in a 10 L reaction flask and stirred in suspension. 34.8 g (0.36 mol) of sulfuric acid were slowly added dropwise at room temperature until the reaction solution was clear, and the reaction continued for 30 min with stirring. Insolubles were removed by filtration, and the filtrate was concentrated under reduced pressure to dryness to obtain 135 g to 168 g of the desired product (yield: 80 to 90%).

MS m/z (ESI): 415.1651[M+1].
$^1$H NMR (400 MHz, DMSO-d$_6$): δ 12.75 (s, 1H), 11.04 (s, 1H), 8.37 (s, 1H), 7.41-7.42 (t, 1H), 6.89 (s, 1H), 5.15-5.19 (m, 1H), 3.89 (s, 3H), 3.68-3.70 (m, 2H), 3.38-3.40 (m, 2H), 3.29 (s, 3H), 2.95 (s, 2H), 2.09-2.16 (m, 2H), 1.92-1.97 (m, 2H).

Example 2: Crystal Form Measurement of the Sample of Example 1

Figure 3:
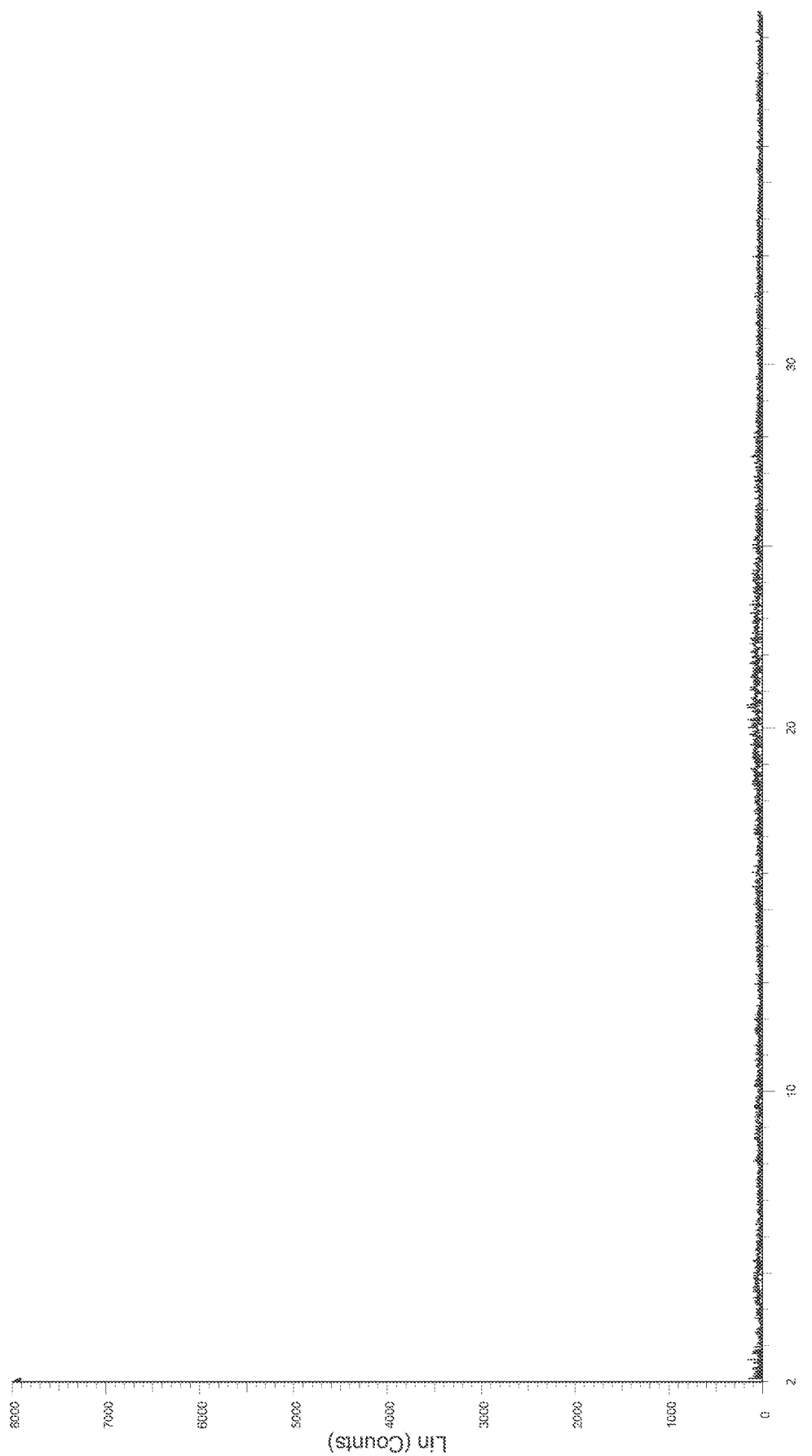
FIG. 3 shows the X-ray powder diffraction spectrum of amorphous solid of the compound of formula (I)
Figure 4:
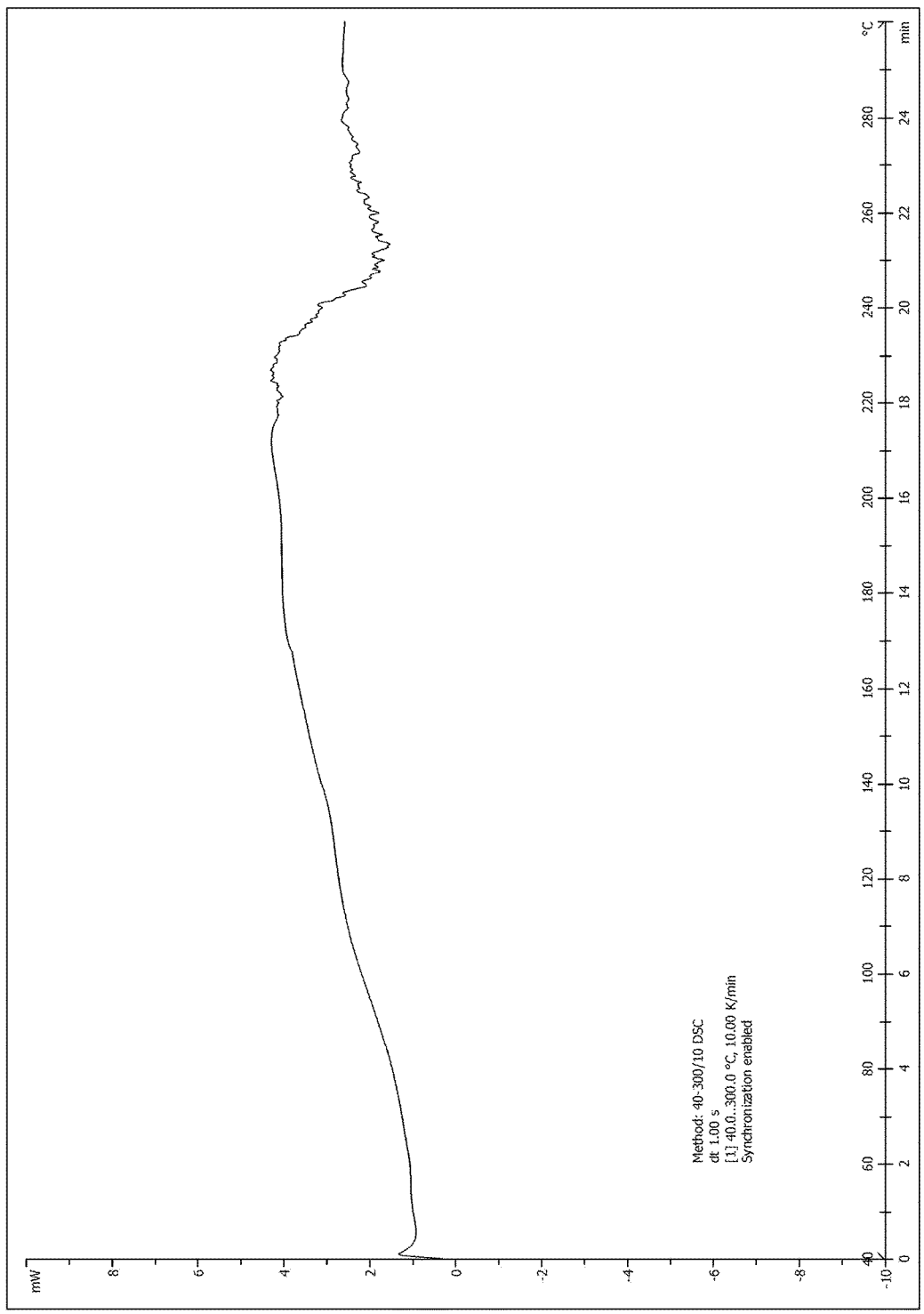
FIG. 4 shows the DSC spectrum of amorphous solid of the compound of formula (I).

The X-ray diffraction spectrum of the solid sample prepared in Example 1 is shown in FIG. 3 in which there are no characteristic absorption peaks of a crystal. The DSC spectrum of this solid sample is shown in FIG. 4, which has no melting characteristic absorption peak below 300° C. The product was thus identified as an amorphous solid.

Example 3

Figure 1:
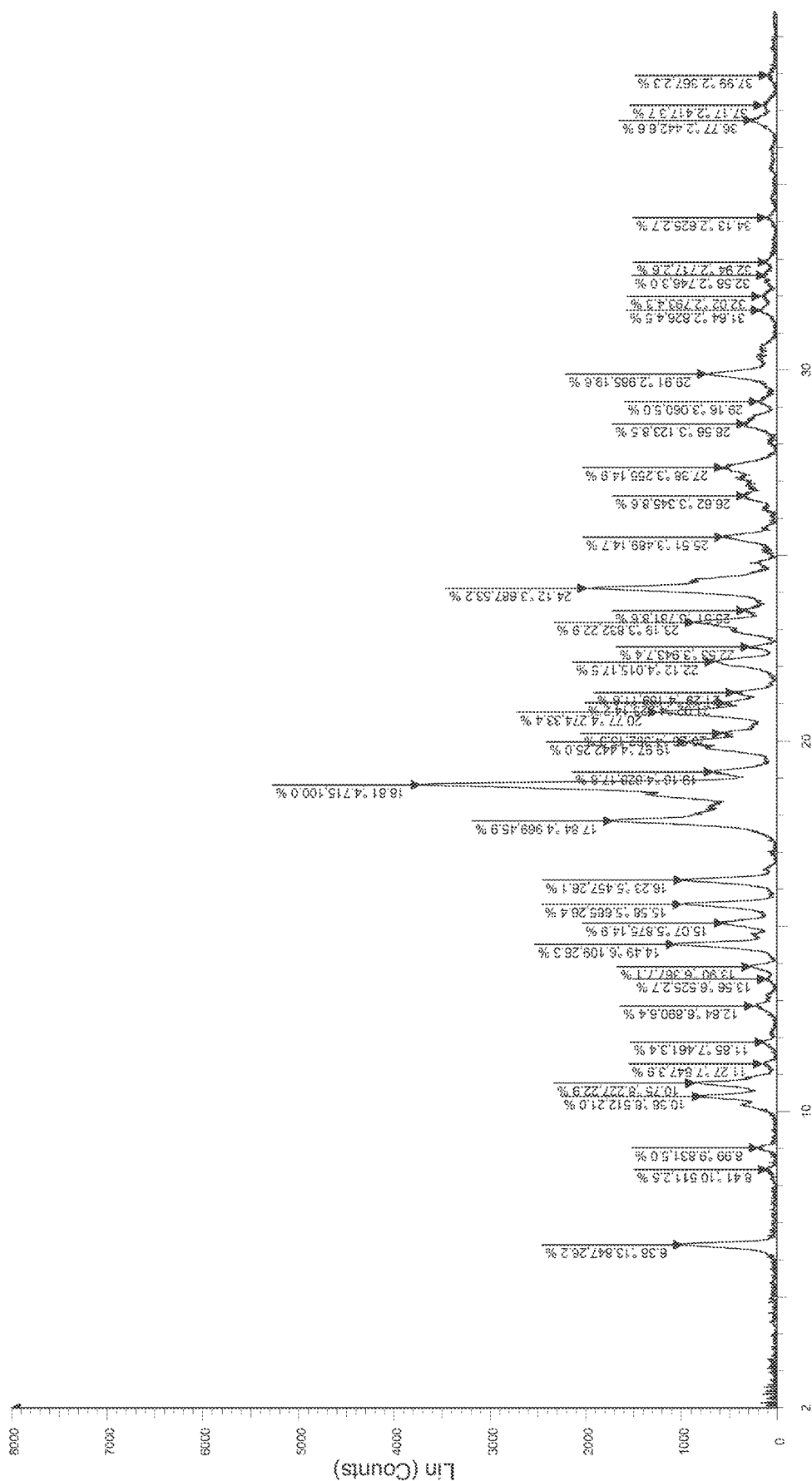
FIG. 1 shows the X-ray powder diffraction spectrum of crystal form I of the compound of formula (I) (represented by the symbol SHR0302 in the figure)
Figure 2:
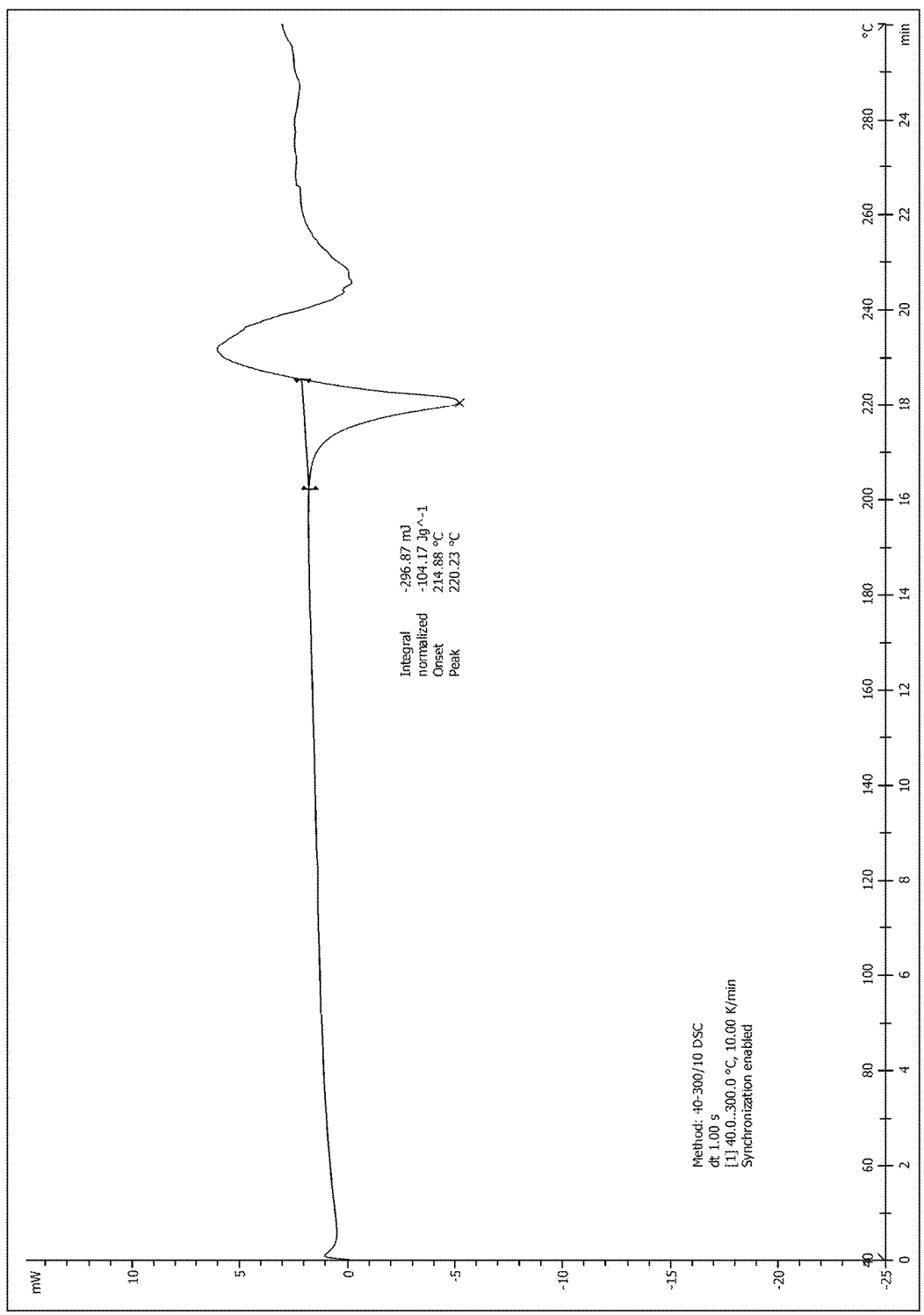
FIG. 2 shows the DSC spectrum of crystal form I of the compound of formula (I)

1.0 g (2.4 mmol) of the compound of formula (I) (prepared according to the method of Example 1) and 100 ml of methanol were added to a 250 ml one-necked flask, and heated to reflux until the solution was clear, then the solution was refluxed for another 10 min. About 90 ml of methanol were removed by evaporation at atmospheric pressure, and a large amount of white solid was precipitated. The mixture was filtered while it was hot, and dried to obtain 784 mg of a white solid in 78.4% yield. The X-ray diffraction spectrum of this crystal sample is shown in FIG. 1 in which there are characteristic peaks at 6.38 (13.85), 10.38 (8.51), 10.75 (8.23), 14.49 (6.11), 15.07 (5.88), 15.58 (5.69), 16.23 (5.46), 17.84 (4.97), 18.81 (4.72), 19.97 (4.44), 20.77 (4.27), 22.12 (4.02), 23.19 (3.83), 24.12 (3.69), 25.51 (3.49), 26.62 (3.35), 27.38 (3.26), 28.56 (3.12) and 29.91 (2.99). The DSC spectrum of this crystal sample is shown in FIG. 2, having a melting endothermic peak at 220.23° C. This crystal form was defined as crystal form I.

Example 4

The amorphous sample prepared in Example 1 and crystal form I prepared in Example 3 were spread flat in the air to test their stability under the conditions of lighting (4500 Lux), heating (40° C., 60° C.), and high humidity (RH 75%, RH 90%). Sampling times of 5 days and 10 days were studied, and the purity as detected by HPLC is shown in Table 1.

TABLE 1

Comparison of stability of crystal form I and amorphous sample of the compound of formula (I)

| Batch number | Time (Day) | Lighting | 40° C. | 60° C. | RH 75% | RH 90% |
|---|---|---|---|---|---|---|
| Crystal form I | 0 | 99.45% | 99.45% | 99.45% | 99.45% | 99.45% |
| S011113120828 | 5 | 99.40% | 99.42% | 99.36% | 99.42% | 99.42% |
|  | 10 | 99.39% | 99.42% | 99.35% | 99.40% | 99.39% |
| Amorphous | 0 | 98.33% | 98.33% | 98.33% | 98.33% | 98.33% |
| Form 20120918 | 5 | 98.04% | 97.65% | 94.53% | 98.32% | 99.14% |
|  | 10 | 97.51% | 96.61% | 92.12% | 98.16% | 99.12% |

After crystal form I and the amorphous sample of the compound of formula (I) were spread flat in the air to test the stability under the conditions of lighting, high temperature, and high humidity, the results of the stability study showed that high humidity does not have much effect on the two examples, but under the conditions of lighting and high temperature, the stability of crystal form I is significantly better than that of the amorphous sample.

What is claimed is:

1. Crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate, wherein the crystal has a characteristic X-ray powder diffraction (XRPD) spectrum comprising diffraction peaks at angles (2θ) of about 17.84, 18.81, and 24.12.

2. A method of preparing crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1, comprising:
   (a) dissolving a first solid of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate in any crystal form or amorphous form into an organic solvent under heating, then evaporating a portion of the organic solvent at atmospheric pressure to precipitate a second solid, wherein the organic solvent is an alcohol having 3 or less carbon atoms; and
   (b) filtering the second solid, then washing and drying the second solid to thereby obtain the crystal form I.

3. The preparation method according to claim 2, wherein the organic solvent in step (a) is methanol.

4. A pharmaceutical composition comprising crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1 and a pharmaceutically acceptable carrier.

5. The pharmaceutical composition according to claim 4, wherein an amount of crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate in the pharmaceutical composition is 0.5 mg to 200 mg.

6. The pharmaceutical composition according to claim 4, wherein the pharmaceutically acceptable carrier is at least one selected from the group consisting of lactose, mannitol, microcrystalline cellulose, croscarmellose sodium, sodium carboxymethyl starch, hydroxypropyl methyl cellulose, povidone, and magnesium stearate.

7. The crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1, wherein the crystal has a differential scanning calorimetry (DSC) spectrum comprising an endothermic melting peak at about 220.23° C.

8. Crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate, wherein the crystal has an X-ray powder diffraction (XRPD) spectrum as shown in FIG. 1.

9. The crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1, wherein the characteristic XRPD spectrum further comprises peaks at diffraction angles:

| Angle (2θ) | d-value (Angstrom) |
|---|---|
| about 6.38 | about 13.85 |
| about 10.38 | about 8.51 |
| about 10.75 | about 8.23 |
| about 14.49 | about 6.11 |
| about 15.07 | about 5.88 |
| about 15.58 | about 5.69 |
| about 16.23 | about 5.46 |
| about 19.97 | about 4.44 |
| about 20.77 | about 4.27 |
| about 22.12 | about 4.02 |
| about 23.19 | about 3.83 |
| about 25.51 | about 3.49 |
| about 26.62 | about 3.35 |
| about 27.83 | about 3.26 |
| about 28.56 | about 3.12 |
| about 29.91 | about 2.99. |

10. A pharmaceutical composition comprising crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 8 and a pharmaceutically acceptable carrier.

11. A method of treating a Janus kinase (JAK)-related disease in a subject in need thereof, the method comprising administering to the subject the pharmaceutical composition of claim 4, wherein the JAK-related disease is rheumatic arthritis or rheumatoid arthritis.

12. A method of treating a Janus kinase (JAK)-related disease in a subject in need thereof, the method comprising administering to the subject the pharmaceutical composition of claim 10, wherein the JAK-kinase related disease is rheumatic arthritis or rheumatoid arthritis.

13. A pharmaceutical composition comprising crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 7 and a pharmaceutically acceptable carrier.

14. A pharmaceutical composition comprising crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 9 and a pharmaceutically acceptable carrier.

15. A method of treating a Janus kinase (JAK)-related disease in a subject in need thereof, the method comprising administering to the subject the pharmaceutical composition of claim 13, wherein the JAK-related disease is rheumatic arthritis or rheumatoid arthritis.

16. A method of treating a Janus kinase (JAK)-related disease in a subject in need thereof, the method comprising administering to the subject the pharmaceutical composition of claim 15, wherein the JAK-related disease is rheumatic arthritis or rheumatoid arthritis.

17. The crystal form I of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1, wherein the crystal has the following d-values (angstrom) at the indicated diffraction angles ($2\theta$):

| Angle ($2\theta$) | d-value (Angstrom) |
|---|---|
| about 17.84 | about 4.97 |
| about 18.81 | about 4.72 |
| about 24.12 | about 3.69. |

* * * * *